United States Patent
Freeman et al.

(10) Patent No.: US 10,595,562 B2
(45) Date of Patent: Mar. 24, 2020

(54) INHALATION DEVICE WITH METERING

(71) Applicant: INDOSE INC, Woodland Hills, CA (US)

(72) Inventors: Daniel Freeman, Agoura, CA (US); Ari Freeman, Lafayette, CA (US); Jacqueline Freeman, Lafayette, CA (US)

(73) Assignee: INDOSE INC, Woodland Hills, CA (US)

( * ) Notice: Subject to any disclaimer, the term of this patent is extended or adjusted under 35 U.S.C. 154(b) by 0 days.

(21) Appl. No.: 15/244,518

(22) Filed: Aug. 23, 2016

(65) Prior Publication Data
US 2017/0156399 A1 Jun. 8, 2017

Related U.S. Application Data

(60) Provisional application No. 62/386,614, filed on Dec. 7, 2015, provisional application No. 62/386,615, filed (Continued)

(51) Int. Cl.
*A24F 47/00* (2020.01)
*F22B 1/28* (2006.01)
(Continued)

(52) U.S. Cl.
CPC ....... *A24F 47/008* (2013.01); *A61M 15/0065* (2013.01); *A61M 15/0086* (2013.01);
(Continued)

(58) Field of Classification Search
CPC ...... A24F 47/008; A24F 47/002; G01F 1/661; G01F 1/34; G01F 1/66; G01F 23/292;
(Continued)

(56) References Cited

U.S. PATENT DOCUMENTS 5,881,715 A * 3/1999 Shibasaki ......... A61M 15/0085
128/200.14
9,072,321 B2 7/2015 Liu
(Continued)

FOREIGN PATENT DOCUMENTS

GB 2430252 A * 3/2007 ........ A61M 15/0065
GB 2524779 A 10/2015
(Continued)

OTHER PUBLICATIONS

Communication from the Australian Patent Office dated Jul. 4, 2019, in Application No. 2017316131 (3 pages total).
(Continued)

*Primary Examiner* — Timothy A Stanis
*Assistant Examiner* — Victoria Murphy
(74) *Attorney, Agent, or Firm* — Sughrue Mion, PLLC; Richard C. Turner

(57) ABSTRACT

An inhalation device for inhaling a vaporized substance that includes metering capabilities to inform a user when a particular amount of substance has been consumed. The inhalation device can include a sensor that senses the vaporized substance and a processor that utilizes data from the sensor to meter the amount consumed. The inhalation device can also define a session, which is a time in which a user can consume a particular amount. During the session, a user can start and stop inhaling and resume inhaling. When the user stops inhaling the inhalation device will halt vapor production and will resume production when the user resumes inhaling.

1 Claim, 8 Drawing Sheets

Related U.S. Application Data on Dec. 7, 2015, provisional application No. 62/388,066, filed on Jan. 13, 2016.

(51) Int. Cl.
   *G01N 30/00* (2006.01)
   *G01N 21/85* (2006.01)
   *A61M 15/00* (2006.01)
   *A61M 15/06* (2006.01)
   *G01N 15/06* (2006.01)
   *A61M 16/00* (2006.01)
   *A61M 11/04* (2006.01)

(52) U.S. Cl.
   CPC ............ *A61M 15/06* (2013.01); *F22B 1/284* (2013.01); *G01N 21/85* (2013.01); *G01N 30/00* (2013.01); *A61M 11/042* (2014.02); *A61M 15/0001* (2014.02); *A61M 2016/0021* (2013.01); *A61M 2016/0027* (2013.01); *A61M 2016/0039* (2013.01); *A61M 2205/3653* (2013.01); *G01N 2015/0693* (2013.01); *G01N 2021/8578* (2013.01)

(58) Field of Classification Search
   CPC ............ G01F 23/2922; G01F 23/2928; A61M 15/001; A61M 15/0065; A61M 2016/0003; A61M 2016/003; A61M 2016/0033; A61M 15/0001; A61M 2016/01
   USPC .................................................... 128/200.23
   See application file for complete search history.

(56) References Cited

U.S. PATENT DOCUMENTS

| | | |
|---|---|---|
| 2004/0089314 A1 | 5/2004 | Felter et al. |
| 2005/0016550 A1 | 1/2005 | Katase |
| 2005/0068528 A1* | 3/2005 | Altobelli .................. A61B 5/08 356/338 |
| 2005/0072421 A1* | 4/2005 | Suman .................. A61M 15/00 128/200.23 |
| 2005/0247312 A1* | 11/2005 | Davies .............. A61M 15/0045 128/203.15 |
| 2008/0017197 A1* | 1/2008 | Kaneko .................. A61M 11/00 128/203.12 |
| 2010/0307518 A1 | 12/2010 | Wang |
| 2010/0313901 A1 | 12/2010 | Fernando et al. |
| 2011/0265806 A1 | 11/2011 | Alarcon et al. |
| 2013/0192595 A1* | 8/2013 | Tolmie .................. A61M 16/12 128/202.22 |
| 2013/0276799 A1* | 10/2013 | Davidson .............. A24F 47/004 131/273 |
| 2014/0069424 A1* | 3/2014 | Poston .................. A24F 47/008 128/202.21 |
| 2015/0216237 A1 | 8/2015 | Wensley et al. |

FOREIGN PATENT DOCUMENTS

| | | |
|---|---|---|
| WO | 2011033396 A2 | 3/2011 |
| WO | 2016/039625 A1 | 3/2016 |
| WO | 2016/101203 A1 | 6/2016 |

OTHER PUBLICATIONS

Written Opinion in International Application No. PCT/US2017/019033, dated Nov. 27, 2017 (12 pages total).

International Search Report on International Application No. PCT/US2017/019033, dated Nov. 27, 2017 (4 pages total).

* cited by examiner

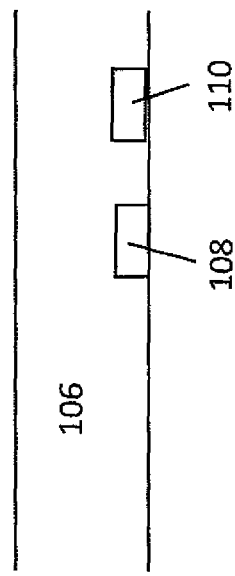

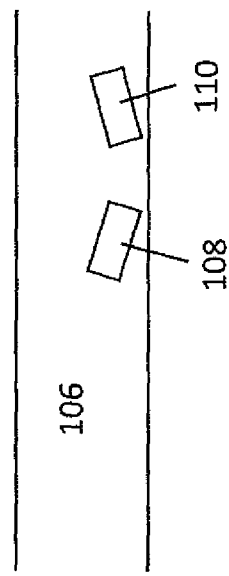

INHALATION DEVICE WITH METERING

RELATED APPLICATION DATA

This application claims priority from U.S. Provisional Patent Application Nos. 62/386,614 and 62/386,615, both of which were filed on Dec. 7, 2015, and 62/388,066, which was filed on Jan. 13, 2016. These applications are incorporated by reference herein.

BACKGROUND

Inhaling devices such as vaporizers, vaporizing pens, and vaporizing machines are used to vaporize substances such as tobaccos, oils, liquids, medical drugs, and plant herbs. Once vaporized, these substances are then inhaled by consumers. Such inhaling devices have health benefits over traditional smoking methods. But inhaling the vapor can have negative effects on the body depending on the substance, such as nicotine. Inhaling devices have become more popular with consumers, but pose problems.

For example, while vaporizers can be safer than traditional smoking methods, it is difficult to meter the amount of vaporized substance that is being inhaled. So a user of an inhalation device that vaporizes nicotine may actually consume more nicotine than had the user smoked cigarettes or cigars.

There are multiple factors that affect the quantity of drug that is inhaled. These factors include the drug concentration of the vaporized substance, the amount of vapor inhaled, the duration of inhalation, variations between inhalation devices, and variation and inconsistency in the functionality of the device.

Another issue is that the inhaled substances may have different effects on different users depending on various factors. To optimize a user's experience, it is necessary' to track the quantity inhaled taken over time and track the resulting effect it has on that user. This can be a tedious and demanding task. Typical users may not keep track of each dose and record the experience.

SUMMARY

In one aspect, this disclosure describes an inhalation device for inhaling a vaporized substance that includes a channel through which the vaporized substance can flow, a light signal device, wherein the light signal device emits light; a sensor, wherein the sensor senses the light from the light signal device; and wherein the light signal device and the sensor are positioned in the channel such that the vaporized substance can flow past the sensor and the light signal device.

In another aspect, this disclosure also describes a processor, wherein said processor uses data from the sensor to meter the consumption of the vaporized substance. The inhalation device can also include a sensor, wherein the sensor acquires data relating to airflow in the device. The inhalation device can further include an indicator, wherein the indicator informs the user when a dose of the substance has been inhaled.

In another aspect, this disclosure describes an inhalation device for inhaling a vaporized substance comprising a processor; and a meter, wherein the meter comprises an indicator; wherein the processor, using data from the timer, calculates the amount of the substance inhaled, and wherein the indicator informs the user of the amount that has been inhaled. The inhalation device can further include a mouthpiece, from which a user can inhale a vaporized substance; a reservoir, wherein the substance in unvaporized form is stored; and a heating element, wherein said heating element is used to heat the unvaporized substance.

The inhalation device can also have the capability of the meter indicating a progressive inhalation of the substance including a progressive inhalation of the substance in discrete quantities.

Metering Dosage

This could be any combination or stand-alone of: time measurements, an air flow sensor, mass flow sensor, volume/measurement sensor for air, volume/measurement sensor for the medication/drug, a heat sensor, current measurements, voltage measurements, vapor analyzer, vapor concentration sensor, or vapor contents sensor.

Other methods of detecting airflow may include pressure sensors, microphones as pressure sensors, microphones as sound sensors to detect air flow (for example by detecting a whistle sound of the air). And several other methods of measuring air flow directly or indirectly. Some specific examples of sensors that may be used are:

- Air pressure sensors setup to measure the pressure at various positions in the inhale tube. These measurements can be compared to each other and based on the distance between the sensors and diameter of tube, we can determine airflow rate and/or volume. A propeller may be set in the tube that would spin according to air speed. The frequency of revolutions could be measured and used to calculate air speed.
- A microphone may be setup inside the inhale tube to listen to the white noise of the air passing through. A correlation may be made between the sound intensity and/or frequency to the airflow rate.
- The above information would be combined with known vaporization characteristics of the vape, vapor characteristics and or other measured data (time for example) and then a determination may be made about the drug dosage of the inhale.
- Using some of the above inputs the system could calculate/display the amount of drug intake. Alternatively, the system could be set to stop dispensing the drug once a certain dose is reached.
- The vaporizer unit may be designed so that the airflow rate is known by design. For example, the design may limit the flow rate by restricting the airflow to a known airflow rate, perhaps by directing the flow thru a narrow channel. In such as case, the airflow rate would be known and direct airflow rate measurements may not be needed. Rather, the known airflow rate could be combined with other factors, such as duration (time) of inhale and other vaporization characteristics, to determine the quantity of drug consumed.

The measured information may be combined with specific characteristics of the vaporizer unit to determine consumption information. For example: A flow rate of 20 cubic-cm/second combined with an inhale duration of 3 seconds will result in a 60 cubic-cm volume intake. This information may be combined with a drug-vapor-density factor (such as 1 mg drug/100 cubic-cm) to determine the quantity of drug consumed (in this case 0.6 mg of drug).

Further accuracy may be achieved by incorporating information regarding the vaporization element, such as current, voltage, startup time delays and so on.

- Other methods of metering could include metering of the un-vaporized drug. Possibly metering the delivery from the cartridge to the heating chamber.

Examples of such embodiments may include:
- A metered valve to monitor the drug delivered from storage to heating area.
- An optical sensor configured to measure the remaining drug in the chamber.
- Weight measurements can be taken to compare pre and post-delivery weights of the drug.

In another aspect; this disclosure describes an inhalation device comprising: a body, wherein the body includes: a mouthpiece, from which a user can inhale a vaporized substance; a reservoir, wherein the substance in unvaporized form is stored; a heating element, wherein said heating element is used to heat the unvaporized substance; and a processor, wherein the processor defines a session; wherein the device is configured such that the unvaporized substance from the reservoir is heated by the heating element to create a vaporized substance and said vaporized substance is inhaled by the user through the mouthpiece; and wherein the processor is configured to keep a session open, during which the processor is configured to stop the heating element when the user stops inhaling, and is configured to start the time and the heating element when the user resumes inhaling.

DESCRIPTION OF THE DRAWINGS

FIG. 1A is a diagram of a portion of an inhalation device.

FIG. 1B is another diagram of a portion of an inhalation device.

DETAILED DESCRIPTION

Figure 1:
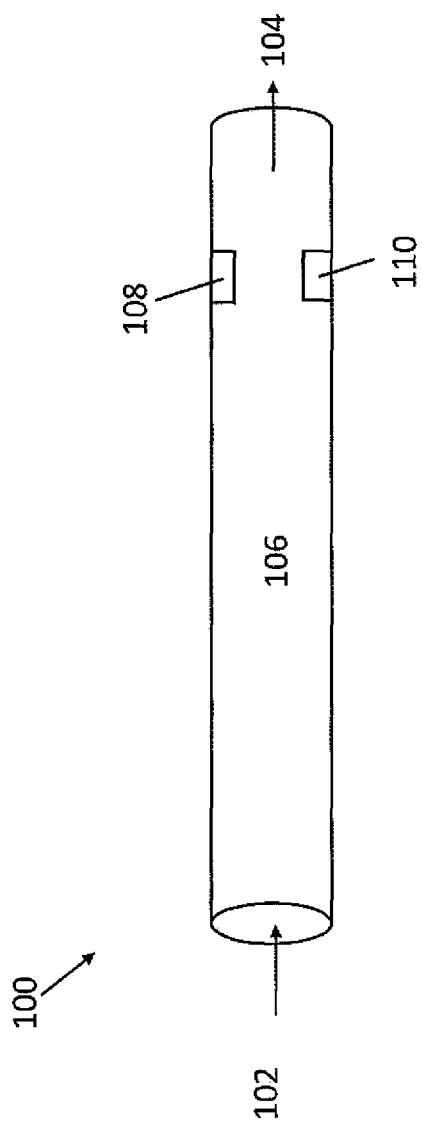
FIG. 1 is a diagram of an inhalation device.

FIG. 1 illustrates an inhalation device 100 for inhaling a vaporized substance. The inhalation device 100 includes a first opening 102 and a second opening 104. In between the two openings is a channel 106. When a user inhales using the inhalation device 100, air flows into the first opening 102 and in the device 100, vaporized substance is created by a heating element (not shown), and a mixture of air and vapor flows through the channel 106 to the second opening 104 and ultimately to the user.

The inhalation device 100 also includes a sensor 108 and a signal 110. The sensor 108 and signal 110 are positioned across from each other in the channel 106. The sensor 108 senses the vapor amount. For example, the sensor 108 can sense the concentration of vapor. The sensor 108 senses the intensity of the signal emitted by the signal 110. If the sensor 108 senses a high signal output, this indicates that the amount of vapor is low, and the vapor/air mixture is dominated by air. Likewise, if the sensor 108 senses a low signal output, this indicates that the vapor/air mixture is dominated by vapor.

Figure 6:
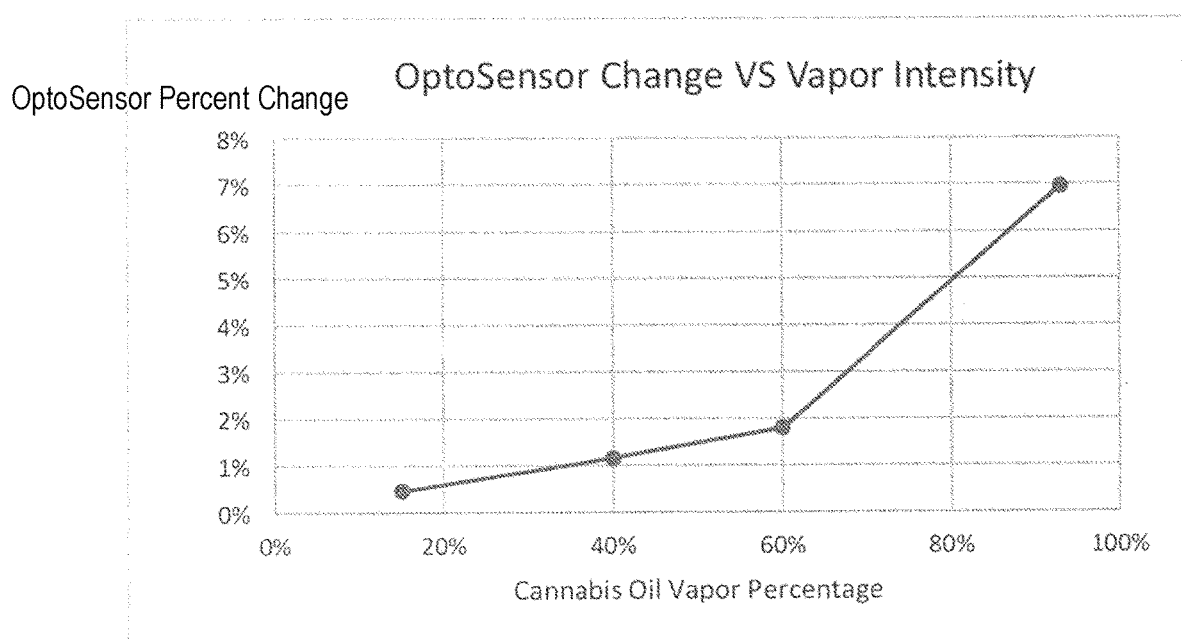
FIG. 6 is a chart showing a relationship between optosensor output and vapor percentage.

Data from the sensor 108 can assist the device 100 in providing information about vapor concentration to the user. For example, if the sensor senses a 5% drop in intensity from the signal 110, that could correlate to a mixture of vapor/air that is 60% vapor. The chart of FIG. 6 graphs the value percent drop in an optocell (i.e., a device that senses the intensity of light) versus the percentage of *cannabis* oil vapor in a mixture of vapor and air:

The chart of FIG. 6 shows the correlation between vapor concentration and the readings from an optocell. Knowing the relative concentration of the vapor can assist the device 100 in providing additional information to the user. For example, if a user inhales using the device 100 and the sensor 108 senses a high output, this may indicate that the concentration is less than expected. The device 100 could include an additional indicator to inform the user that the device 100 is not producing the expected amount of vapor. The sensor 108 can be any suitable sensor that senses light including without limitation, a photosensor, photodetector, optocell, optoresistor, optotransistor, optodi ode, and/or solar ceil. The signal 110 can be any suitable device that produces light, such as an LED. The signal could also emit ultraviolet light. In other words, the signal 110 can produce a wide range of wavelengths of light and the sensor 108 detects those wavelengths of light. The inhalation device 100 can optionally use filters in order to target a specific wavelength of light to optimally detect vapor intensity.

In FIG. 1, the sensor 108 is positioned across from the signal 110. The sensor 108 and the signal 110 can also be positioned in alternative arrangements without departing from the scope of this disclosure. For example, in FIG. 1A the sensor 108 and the signal 110 are positioned next to each other in the channel 106. In another embodiment, shown in FIG. 1B, the sensor 108 and the signal 110 are positioned next to each other at an angle in the channel 106. The arrangements of the sensor 108 and the signal 110 in FIGS. 1A and 1B use concepts of backscatter and fluorescence.

IIn backscatter, the vapor passing through the channel 106 can "reflect" light back from the perspective of the sensor 110. In this scenario, the vapor panicle size would determine the "reflection" properties and angle of refection. In florescence, the light may get absorbed by the vapor particles and a new light may be generated. The new light would then be picked up by the sensor. The light and sensor may be set up facing the same direction (in parallel) towards the channel 106. Other alternative positions of sensor 108 and signal 110 known to persons of ordinary skill in the art whereby the flow of vaporized substance affects the signal received by the sensor from the light produced by the light signal device is intended to fall within the scope of this disclosure. For example, the sensor 108 and the signal 110 may be next to each other but one of the sensor 108 and the signal 110 may also be positioned at an angle.

Figure 2:
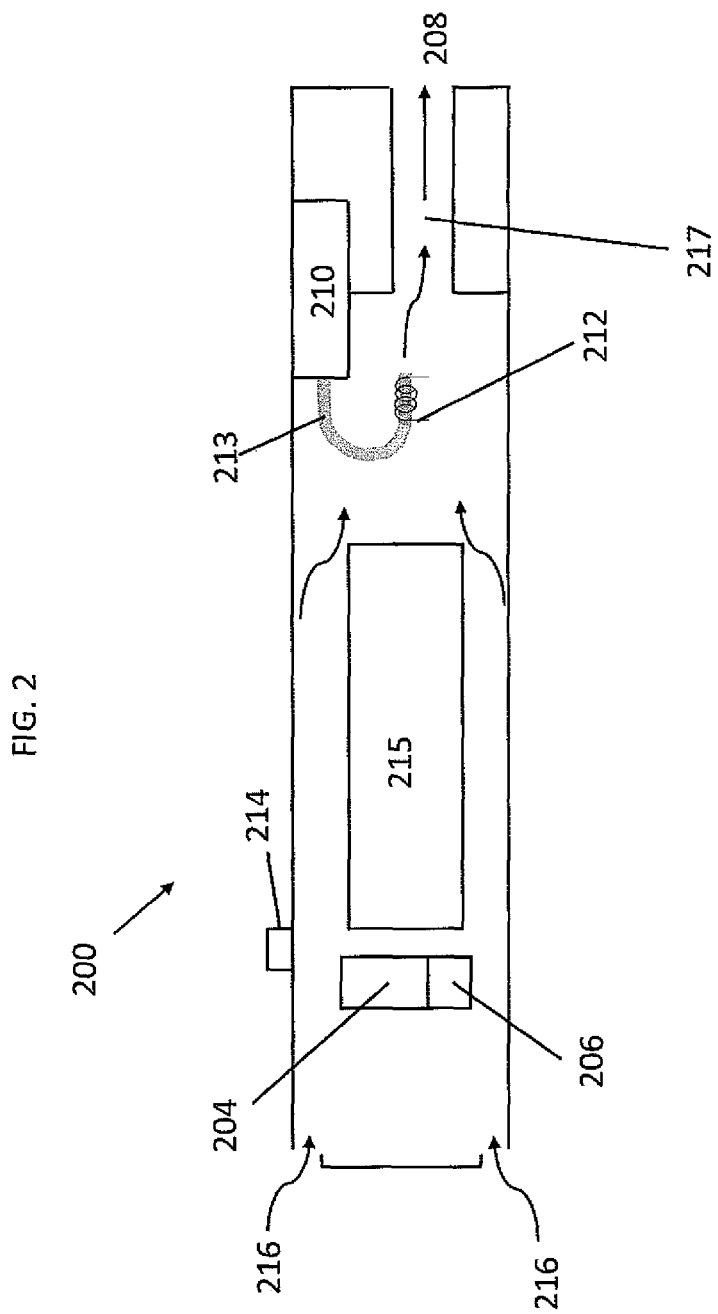
FIG. 2 is another diagram of an inhalation device.

FIG. 2 shows an inhalation device 200. The inhalation device includes a processor 204 and a timer 206. In this embodiment, the inhalation device 200 includes an inlet 216, an outlet 208, a reservoir 210, a heating element 212, and a wick 213. The inhalation device 200 also includes an indicator 214 and a battery 215. The reservoir 210 stores the substance in unvaporized form, and the heating element 212 heats the unvaporized substance from the reservoir 210 via the wick 213 to create a vaporized substance, which is then inhaled by the user through the outlet 208. The device 200 also includes a channel 217 through which the vaporized substance produced by the heating element 212 and air will flow to the outlet 208 when a user inhales.

The device 200 uses the processor 204 and the timer 206 to provide metering information to the user. More specifically, the processor 204 controls the timer 206 such that when a user inhales using the device 200, the processor 204 will start the timer 206 as well as the heating element 212 to begin vaporizing the substance. After the timer 206 has reached a particular value, a particular amount of the vaporized element will have been produced, and the processor 204 will shut off the heating element 212. Alternatively, the processor 204 will not shut off the heating element 212, but rather will send a signal to the indicator 214 that the particular amount of the vaporized element has been consumed.

For example, if the heating element produces 1 mg/second, and the particular amount is 3 mg, the processor will turn on the heating element 212 when a user inhales, and the processor will turn off the heating element when the timer reaches 3 seconds. After the timer reaches 3 seconds, the processor will send a signal to the indicator 214, which will then indicate that the particular amount has been consumed. The indicator 214 can be an audio signal, visual signal, visual display, or a vibration. The indicator 214 could also be a transmitter that sends a signal to an external device such as a smart phone, tablet, or computer indicating that a particular amount has been consumed.

Figure 5:
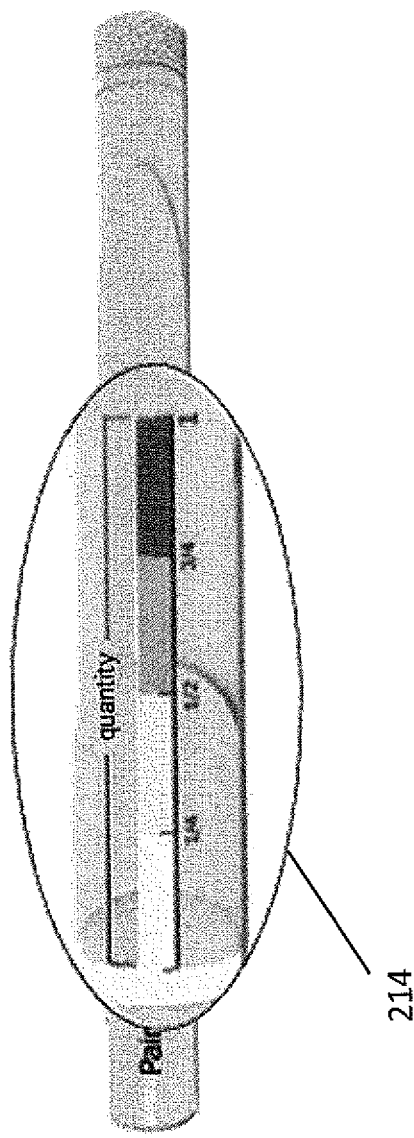
FIG. 5 is another diagram of an inhalation device.

Alternatively, the indicator 214 could display what amount the user has consumed. As shown in FIG. 5, as a visual indicator to the user, the indicator 214 may include a progressive meter indicator. This could take the form of a sequence of lights, possibly LED lights, which indicate the progression of the amount consumed by the user. For example, there could be a sequence of four LED lights on the vaporizer indicating when a 14, ½, ¾ and full amount has been taken. When the full amount has been taken, the lights might be programmed to indicate to the user that the full amount has been reached by flashing. The progressive meter indicator could take other forms, like a mechanical indicator, a dial, a screen display, or a sound sequence. The progressive meter indicator may continue to meter and indicate the user beyond one cycle. For example, after a full amount has been taken the indicator will turn all lights off and begin turning on each light again as the user consumes.

In the above example, in which a particular amount is set at 3 mg and the heating element 212 produces 1 mg/second of vapor, 3 mg will be delivered to a user who inhales for 3 seconds. In the event that the user cannot inhale long enough to consume a single dose in a single inhalation, the device 200 is configured to keep a session open, with a session being defined as a particular time within which a can consume the particular amount. A session in this case could be set to 10 seconds. In this open session configuration, the device 200 can stop producing vapor when the user stops inhaling and start producing vapor when the user inhales again. When the sum of the user's inhalations amounts to consumption of 3 mg, the processor will send a signal to the indicator 214. Determining when the user stops inhaling can be achieved by using a pressure sensor. Where the pressure drops below a threshold, the heating element will stop. And when the pressure goes above the threshold, the heating element will resume. Alternatively, instead of time-based, a session can be vapor-based, where the device 200 keeps a session open until a certain quantity of vapor is produced.

Figure 3:
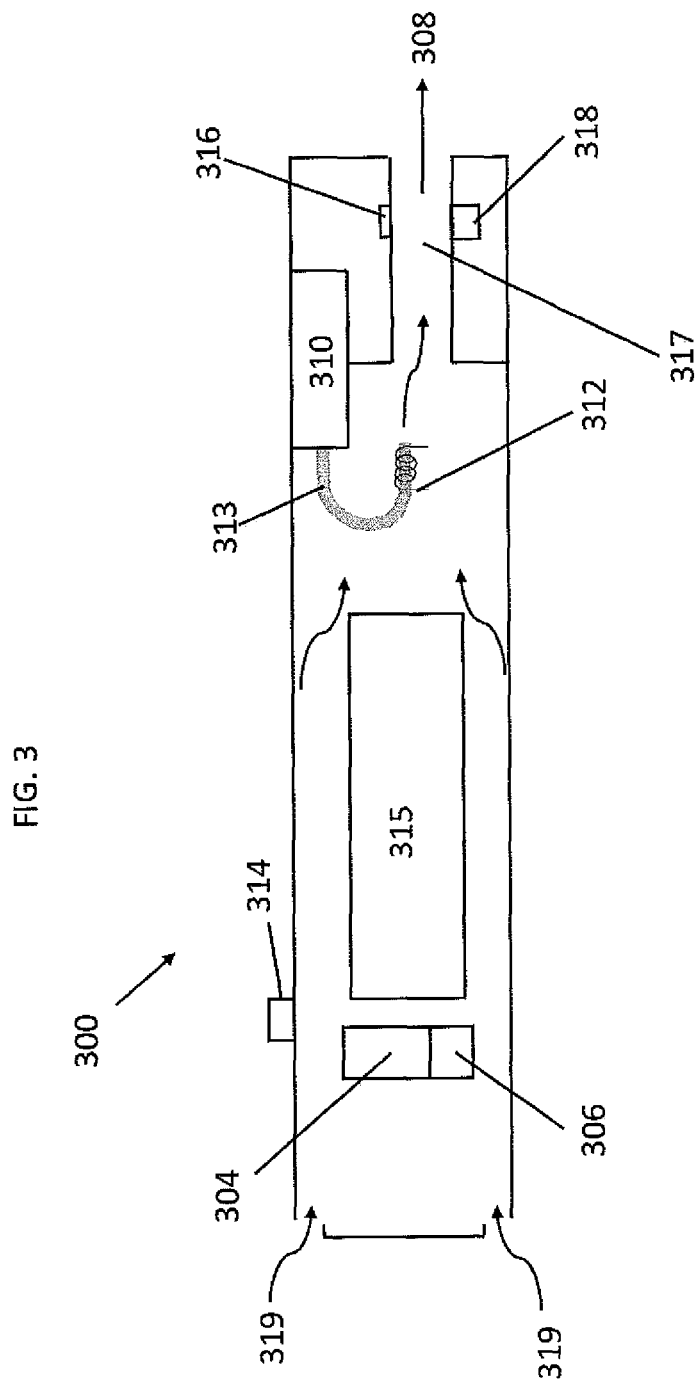
FIG. 3 is another diagram of an inhalation device.

FIG. 3 shows an inhalation device 300 according to another embodiment. The inhalation device includes a processor 304 and a timer 306. In this embodiment, the inhalation device 300 includes an inlet 319, an outlet 308, a reservoir 310, a heating element 312, and a wick 313. The inhalation device 300 also includes an indicator 314 and a battery 315. The reservoir 310 stores the substance in unvaporized form, and the heating element 312 heats the unvaporized substance from the reservoir 310 via the wick 313 to create a vaporized substance. which is then inhaled by the user through the outlet 308. The device 300 also includes a channel 317 through which the vaporized substance produced by the heating element 312 and air will flow to the outlet 308 when a user inhales.

The device 300 further includes an indicator 314 that will indicate to the user when a particular amount of the vaporized substance has been consumed. The indicator 314 can be an audio signal, visual signal, visual display, or a vibration. The indicator 314 could also be a transmitter that sends a signal to an external device such as a smart phone, tablet, or computer indicating that a dose has been consumed. Alternatively, the indicator 314 could display what dose the user has consumed.

The inhalation device 300 can also include a sensor 316 and a signal 318, such as an LED that produces a wide range of light wavelengths. The signal could also be one that produces ultraviolet light. The sensor 316 and signal 318 are positioned across from each other in the channel 317. The sensor 316 senses the concentration of the vapor. For example, the sensor 316 can be an optical sensor that senses the intensity of the light produced by the signal 318. If the sensor 316 senses a high output, this indicates that the vapor concentration is low, and the vapor/air mixture is mostly, if not all, air. If the sensor 316 senses a low output, this indicates that the vapor concentration is high. The processor 304 records information from the sensor 316. The sensor 316 can assist the device 100 in providing information about vapor concentration to the user. For example, if the sensor senses a 5% drop in intensity from the signal 110, that could correlate to a mixture of vapor/air that is 60% vapor.

The processor 304 uses data from the sensor 316 to calculate when a particular amount of the vaporized substance has been produced. This is useful where the substance is viscous such as *cannabis* oil. In such viscous substances the amount of vapor produced for a given time can vary, in the embodiment of FIG. 3, when a user inhales using the device 300, the processor 304 will turn on the heating element 312. The sensor 316 will sense in real time (as a non-limiting example, every 0.1 seconds) the intensity of the light from the signal 318. Using the data from the sensor 316, the processor 304 can determine when a particular amount has been produced.

For example, if a particular amount to be consumed is 3 mg and the heating element 312 vaporizes 1 mg per second, then theoretically the 3 mg should be produced in 3 seconds, in practice, however, it may take longer for the inhalation 300 device to vaporize 3 mg. This may due to factors such as the time it takes the heating element 312 to heat up and the consistency of the drug released from the reservoir 310 to the wick 313. So for example, when a user begins to inhale, the first ten readings of the sensor 316 in the first second (eg., one reading every 0.1 seconds) may indicate that the vapor produced over the first second is 50% of the expected production. This percentage can be thought of as a vapor factor. The processor 304 will take this vapor factor into account to determine when 3 mg is consumed by the user. In other words, the processor 304 will collect the data from the sensor 316 (eg., every 0.1 seconds) on the vapor factor to determine when 3 mg has been consumed by the user. For a given time, the processor 304 will multiply the time (eg., 0.1 seconds) by the vapor factor at that time, and will add each of these products to determine when a particular amount has been consumed. For example, if in the first second of inhalation, 50% of vapor is produced, and assuming 100% of vapor is produced after 1 second; the processor will able to determine that 3 mg has been consumed in 3.5 seconds.

In the above example; the processor 304 is capable of acquiring data from the sensor 316 and also included information on how much a particular amount of substance is expected to be produced per unit of time. The processor 304 can store additional vapor characteristics of the substance. For example, the processor 304 can store the time it takes for the heating element 312 to heat to the temperature at which it vaporizes the substance. The processor 304 can also store the heating and temperature variations during different inhalation profiles. For example, if a user inhales at a high rate, the air flowing through the inlet 319 and into the device 300 can cool the heating element 312. The processor 304 can store information on different rates of inhalation to adjust, for example, the temperature of the heating element 312. The processor 304 can also store information on the flow of drug from the reservoir 310 to the wick 313, the concentration of the substance within a given volume, and the vaporization rates of the substance at different temperatures of the heating element 312. The processor 304 as well as the processors discussed herein can be standard integrated circuit (IC) chips made by IC manufacturers such as Texas Instruments.

Figure 4:
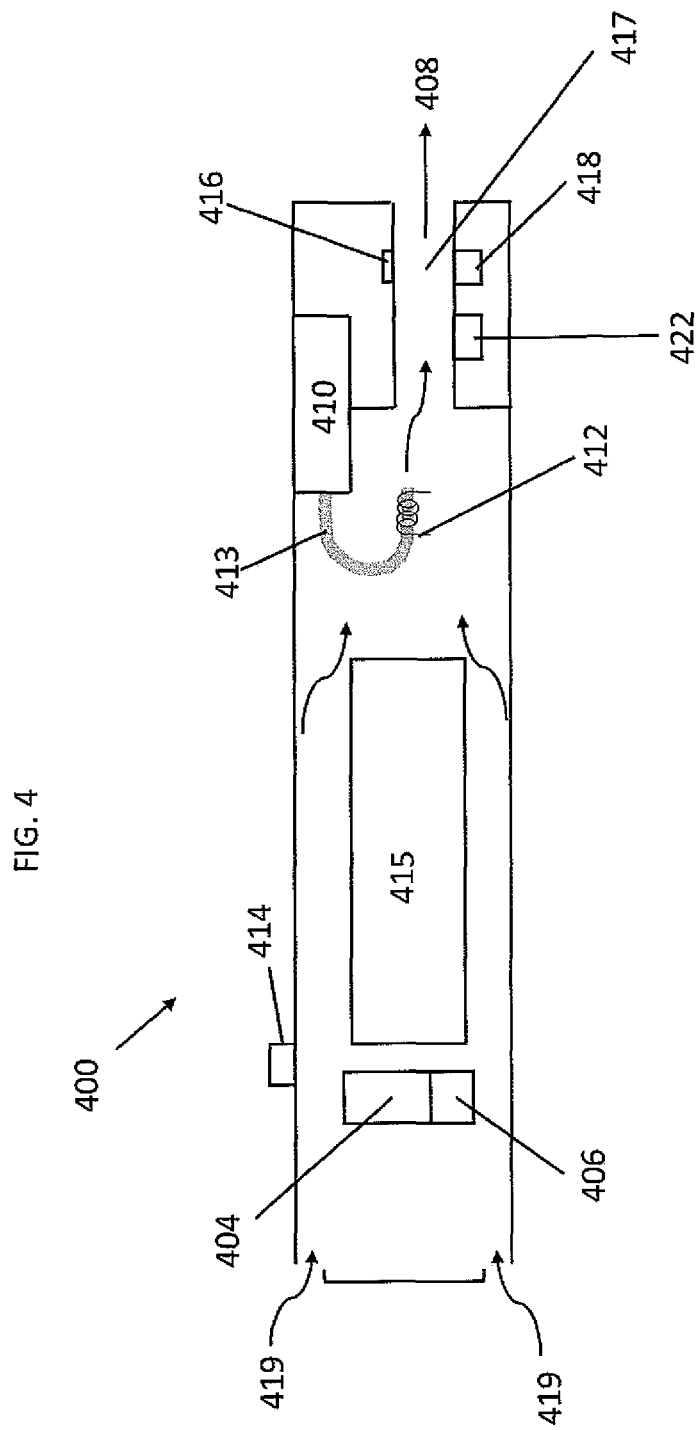
FIG. 4 is another diagram of an inhalation device.

FIG. 4 illustrates another inhalation device 400 according to another embodiment of the disclosure. The inhalation device 400 includes a processor 404 and a timer 406. In this embodiment, the inhalation device 400 includes an inlet 419, an outlet 408, a reservoir 410, a heating element 412, and a wick 413. The device 400 further includes an indicator 414 for informing a user when a dose of the substance has been inhaled. The device 400 also includes a channel 417 through which air and the vaporized substance produced by the heating element 412 flow to the outlet 408 when a user inhales:

The inhalation device 400 also includes a sensor 416 and a signal 418, such as an LED that produces a wide range of light wavelengths. The signal could also be one that produces ultraviolet light. The sensor 416 and signal 418 are positioned across from each other in the channel 417. The sensor 416 senses the concentration of the vapor. For example, the sensor 416 can be an optical sensor that senses the intensity of the light produced by the signal 418 at wavelengths that would include, but not be limited to, visible light and ultraviolet light.

The inhalation device 400 further includes a volume flow sensor 422. The sensor 422 can be any suitable airflow sensor including, but not limited to, any combination or stand-alone of the following: a pressure sensor, a propeller, a microphone or a piezoelectric sensor. The sensor 422 is used to measure the velocity at which the mixture of vapor and air flow through the channel 417. So for example, if the sensor 422 is a propeller, the propeller would be installed in the channel 417 and would spin according to velocity of the vapor/air mixture. The frequency of revolutions can be measured and used to calculate the velocity of the mixture. If the sensor is a microphone, the microphone can be setup in the channel 417 to listen to the noise of the vapor/air mixture passing through the channel. A correlation can be made between the sound intensity and/or frequency to the rate of flow of the mixture. Optionally, the sensor 422 can be placed between the inlet 419 and the processor 404 such that it detects the air flow rate going through the device 400 when a user inhales.

The sensor 422 can be used to adjust the intensity of the heating element 412. The temperature of the heating element can affect the amount of the substance that is vaporized. The sensor 422 is able to sense how intensely a user inhales (i.e., senses the volume per unit time of an inhalation). The processor 404 can acquire this data and adjust the intensity of the heating element by adjusting the voltage of the heating element.

The sensor 422 and the adjustment of the heating element 412 is useful in a non-limiting situation where the user desires to consume a dose more quickly. So for example; if the device 400 is set up so that the heating element produces 1 mg/second of vapor and a dose is 3 mg, a user that inhales at a high volume per unit time can consume the entire dose quicker than 3 seconds. In this scenario, the sensor 422 will be able to sense the higher velocity of the vapor/air mixture, and the processor can increase the intensity of the heating element such that it produces more vapor. The processor 404 can adjust the intensity of the heating element 412 in real time based on data from the sensor 422. So if a user does not inhale intensely, the sensor 422 will detect the decreased flow rate and the processor can then lower the intensity of the heating element 412.

In another embodiment, the inhalation devices described herein can be connected to a mobile device such as a smartphone or tablet and interfaced with a software application. The software application can record the doses that the user has inhaled and record the user's dosage experience. This information can be analyzed by the software to track and optimize the user's experience with the substance inhaled. To help improve analysis, the user could also enter personal information such as ailments, pains, weight and food intake. The information recorded can be used to accurately monitor a user's intake details and may be submitted to a doctor for review and/or improvement.

The application could also connect with other users via the internet. This could be used to share experiences, receive recommendations, and network with a community of users. The application may also be used as an ecommerce platform to purchase dosage capsules, or vaporizer equipment. The platform could offer specific substances based on a user's rated experience. Another enhanced use might be finding other users within geographic locations that may allow for social interactions and meetings. These enhanced services may be integrated with others over the internee.

The vaporizer device could also be locked by the user via the application. This could be used as a safety feature against undesired use (by children or others). There could be locking customizable lock setting to enhance safety or limit usage for those with low self-control.

While embodiments have been described herein with a wick and heating element, other suitable methods of vaporizing a substance could be utilized without departing from the scope of this disclosure. For example, the substance to be vaporized could be placed in a chamber or oven. The oven can be a small cup made of metal, where a user could place the substance. The oven would then heat up and vaporize the substance. Any vapor produced can exit the oven and flow to the user when the user inhales.

While embodiments have been illustrated and described herein, it is appreciated that various substitutions and changes in the described embodiments may be made by those skilled in the art without departing from the spirit of this disclosure. The embodiments described herein are for illustration and not intended to limit the scope of this disclosure.

The invention claimed is:

1. An inhalation device for inhaling a vaporized substance comprising:
    a reservoir, wherein the substance in unvaporized form is stored;
    a heating element, wherein said heating element is used to heat the unvaporized substance;

a processor;
a channel through which the vaporized substance can flow,
a light signal device which emits light;
a first sensor which senses the light from the light signal device; and
a second sensor which measures a quantity related to airflow, wherein the processor uses data from the first and second sensors to dynamically measure, in real-time, the quantity of the substance vaporized and inhaled by the user based on a vapor factor which indicates a percentage of the vaporized substance actually produced during a time period as compared to a theoretical production of vapor yielded during the time period, for each of a plurality of time periods, and adds up the quantities of the substance determined for each of the time periods during an inhalation, to determine when a particular amount of the substance has been consumed.

* * * * *